United States Patent
Cibere

(10) Patent No.: US 10,242,894 B2
(45) Date of Patent: Mar. 26, 2019

(54) SUBSTRATE BREAKAGE DETECTION IN A THERMAL PROCESSING SYSTEM

(71) Applicant: Mattson Technology, Inc., Fremont, CA (US)

(72) Inventor: Joseph Cibere, Burnaby (CA)

(73) Assignee: Mattson Technology, Inc., Fremont, CA (US)

( * ) Notice: Subject to any disclaimer, the term of this patent is extended or adjusted under 35 U.S.C. 154(b) by 0 days.

(21) Appl. No.: 15/909,231

(22) Filed: Mar. 1, 2018

(65) Prior Publication Data

US 2018/0190523 A1 Jul. 5, 2018

Related U.S. Application Data

(62) Division of application No. 15/377,032, filed on Dec. 13, 2016, now Pat. No. 9,941,144.

(Continued)

(51) Int. Cl.
*G01N 25/72* (2006.01)
*G06F 17/50* (2006.01)
(Continued)

(52) U.S. Cl.
CPC ....... *H01L 21/67288* (2013.01); *G01N 25/72* (2013.01); *G06F 17/5009* (2013.01);
(Continued)

(58) Field of Classification Search
None
See application file for complete search history.

(56) References Cited

U.S. PATENT DOCUMENTS 6,065,128 A 5/2000 Harvey
6,204,203 B1 3/2001 Narwankar et al.
(Continued)

FOREIGN PATENT DOCUMENTS

JP 2005-340591 12/2005
JP 2013-247128 12/2013
(Continued)

OTHER PUBLICATIONS

PCT International Preliminary Report on Patentability for Corresponding PCT Application No. PCT/US2016/066345, dated Jul. 12, 2018—7 pages.

(Continued)

*Primary Examiner* — David E Graybill
(74) *Attorney, Agent, or Firm* — Dority & Manning, P.A.

(57) ABSTRACT

Apparatus, systems, and processes for substrate breakage detection in a thermal processing system are provided. In one example implementation, a process can include: accessing data indicative of a plurality of temperature measurements for a substrate, the plurality of measurements obtained during a cool down period of a thermal process; estimating one or more metrics associated with a cooling model based at least in part on the data indicative of the plurality of temperature measurements; and determining a breakage detection signal based at least in part on the one or more metrics associated with the cooling model. The breakage detection signal is indicative of whether the substrate has broken during thermal processing.

5 Claims, 11 Drawing Sheets

Related U.S. Application Data

(60) Provisional application No. 62/272,826, filed on Dec. 30, 2015.

(51) Int. Cl.
  *H01L 21/66* (2006.01)
  *H01L 21/67* (2006.01)
  *H01L 21/324* (2006.01)

(52) U.S. Cl.
  CPC ........ *H01L 21/324* (2013.01); *H01L 21/6719* (2013.01); *H01L 21/67115* (2013.01); *H01L 21/67248* (2013.01); *H01L 22/20* (2013.01)

(56) References Cited

U.S. PATENT DOCUMENTS

| | | | |
|---|---|---|---|
| 6,535,628 B2 | 3/2003 | Smargiassi | |
| 7,442,415 B2 | 10/2008 | Conley, Jr. et al. | |
| 7,446,868 B1 | 11/2008 | Higgs et al. | |
| 7,790,633 B1 | 9/2010 | Tarafdar et al. | |
| 8,323,754 B2 | 12/2012 | Olsen et al. | |
| 8,557,721 B2* | 10/2013 | Timans | H01L 21/67115 257/E23.101 |
| 8,765,492 B2* | 7/2014 | Ono | C30B 29/06 438/14 |
| 8,809,175 B2 | 8/2014 | Tsai et al. | |
| 9,093,468 B2 | 7/2015 | Tsai et al. | |
| 2001/0043735 A1* | 11/2001 | Smargiassi | G06T 7/0008 382/149 |
| 2004/0203254 A1* | 10/2004 | Conley, Jr. | C23C 16/45527 438/778 |
| 2005/0260357 A1* | 11/2005 | Olsen | C23C 16/401 427/569 |
| 2007/0177788 A1 | 8/2007 | Liu | |
| 2008/0242117 A1 | 10/2008 | Ramanarayanan | |
| 2012/0208377 A1 | 8/2012 | Timans | |
| 2012/0012983 A1 | 11/2012 | Ono et al. | |
| 2013/0017678 A1* | 1/2013 | Tsai | H01L 21/28088 438/591 |
| 2014/0264636 A1* | 9/2014 | Tsai | H01L 29/66636 257/408 |
| 2015/0097676 A1 | 4/2015 | Liu et al. | |
| 2015/0140838 A1 | 5/2015 | Kashefi et al. | |
| 2017/0194178 A1 | 7/2017 | Cibere | |

FOREIGN PATENT DOCUMENTS

| | | |
|---|---|---|
| JP | 2015-130423 | 7/2015 |
| WO | WO 2009155117 | 12/2009 |

OTHER PUBLICATIONS

Ragnarsson et al., "The Importance of Moisture Control for EOT Scaling of Hf-Based Dielectrics," *Journal of the Electrochemical Society*, vol. 156, Issue 6, Apr. 3, 2009, pp. H416-H423.

Ferrari et al., "Diffusion Reaction of Oxygen in HfO2/SiO2/Si Stacks," *The Journal of Physical Chemistry B*, vol. 110, No. 30, Jul. 12, 2006, pp. 14905-14910.

Driemeier et al., "Thermochemical behavior of hydrogen in hafnium silicate films on Si," Applied Physics Letters, vol. 89, Issue 5, Aug. 2006,—4 pages.

Driemeier et al., "Room temperature interactions of water vapor with Hf O2 films on Si," Applied Physics Letters, vol. 88, Issue 20, May 2006—3 pages.

Conley, Jr. et al., "Densification and improved electrical properties of pulse-deposited films via in situ modulated temperature annealing," *Applied Physics Letters*, vol. 84, Issue 11, Mar. 15, 2004, pp. 1913-1915.

Nakajima et al., "Experimental Demonstration of Higher-k phase HfO2 through Non-equilibrium Thermal Treatment," ECS Transactions 28.2 (2010), pp. 203-212.

Wu et al., "Device Performance and Reliability Improvement for MOSFETs With HfO2 Gate Dielectrics Fabricated Using Multideposition Room-Temperature Multiannealing," IEEE Electron Device Letters, vol. 32, Issue 9, Sep. 2011, pp. 1173-1175.

PCT International Search Report for corresponding PCT Application No. PCT/US2016/066345, dated Mar. 27, 2017, 3 pages.

\* cited by examiner

SUBSTRATE BREAKAGE DETECTION IN A THERMAL PROCESSING SYSTEM

PRIORITY CLAIM

The present application is a divisional of U.S. application Ser. No. 15/377,032, filed on Dec. 13, 2016, entitled "Substrate Breakage Detection in a Thermal Processing System, which claims the benefit of priority of U.S. Provisional Application Ser. No. 62/272,826, filed Dec. 30, 2015, entitled "Wafer Breakage Detection in a Millisecond Anneal System" which is incorporated herein by reference.

FIELD

The present disclosure relates generally to thermal processing chambers and more particularly to millisecond anneal thermal processing chambers used for processing substrates, for instance, semiconductor substrates.

BACKGROUND

Millisecond anneal systems can be used for semiconductor processing for the ultra-fast heat treatment of substrates, such as silicon wafers. In semiconductor processing, fast heat treatment can be used as an anneal step to repair implant damage, improve the quality of deposited layers, improve the quality of layer interfaces, to activate dopants, and to achieve other purposes, while at the same time controlling the diffusion of dopant species.

Millisecond, or ultra-fast, temperature treatment of semiconductor substrates can be achieved using an intense and brief exposure of light to heat the entire top surface of the substrate at rates that can exceed $10^{4\circ}$ C. per second. The rapid heating of just one surface of the substrate can produce a large temperature gradient through the thickness of the substrate, while the bulk of the substrate maintains the temperature before the light exposure. The bulk of the substrate therefore acts as a heat sink resulting in fast cooling rates of the top surface.

SUMMARY

Aspects and advantages of embodiments of the present disclosure will be set forth in part in the following description, or may be learned from the description, or may be learned through practice of the embodiments.

One example aspect of the present disclosure is directed to a process for breakage detection in a thermal processing system. The process can include: accessing data indicative of a plurality of temperature measurements for a substrate, the plurality of measurements obtained during a cool down period of a thermal process; estimating one or more metrics associated with a cooling model based at least in part on the data indicative of the plurality of temperature measurements; and determining a breakage detection signal based at least in part on the one or more metrics associated with the cooling model. The breakage detection signal is indicative of whether the substrate has broken during thermal processing.

Variations and modification can be made to the example aspects of the present disclosure. Other example aspects of the present disclosure are directed to systems, methods, devices, and processes for breakage detection in a millisecond anneal system.

These and other features, aspects and advantages of various embodiments will become better understood with reference to the following description and appended claims.

The accompanying drawings, which are incorporated in and constitute a part of this specification, illustrate embodiments of the present disclosure and, together with the description, serve to explain the related principles.

BRIEF DESCRIPTION OF THE DRAWINGS

Detailed discussion of embodiments directed to one of ordinary skill in the art are set forth in the specification, which makes reference to the appended figures, in which.

DETAILED DESCRIPTION

Figure 1:
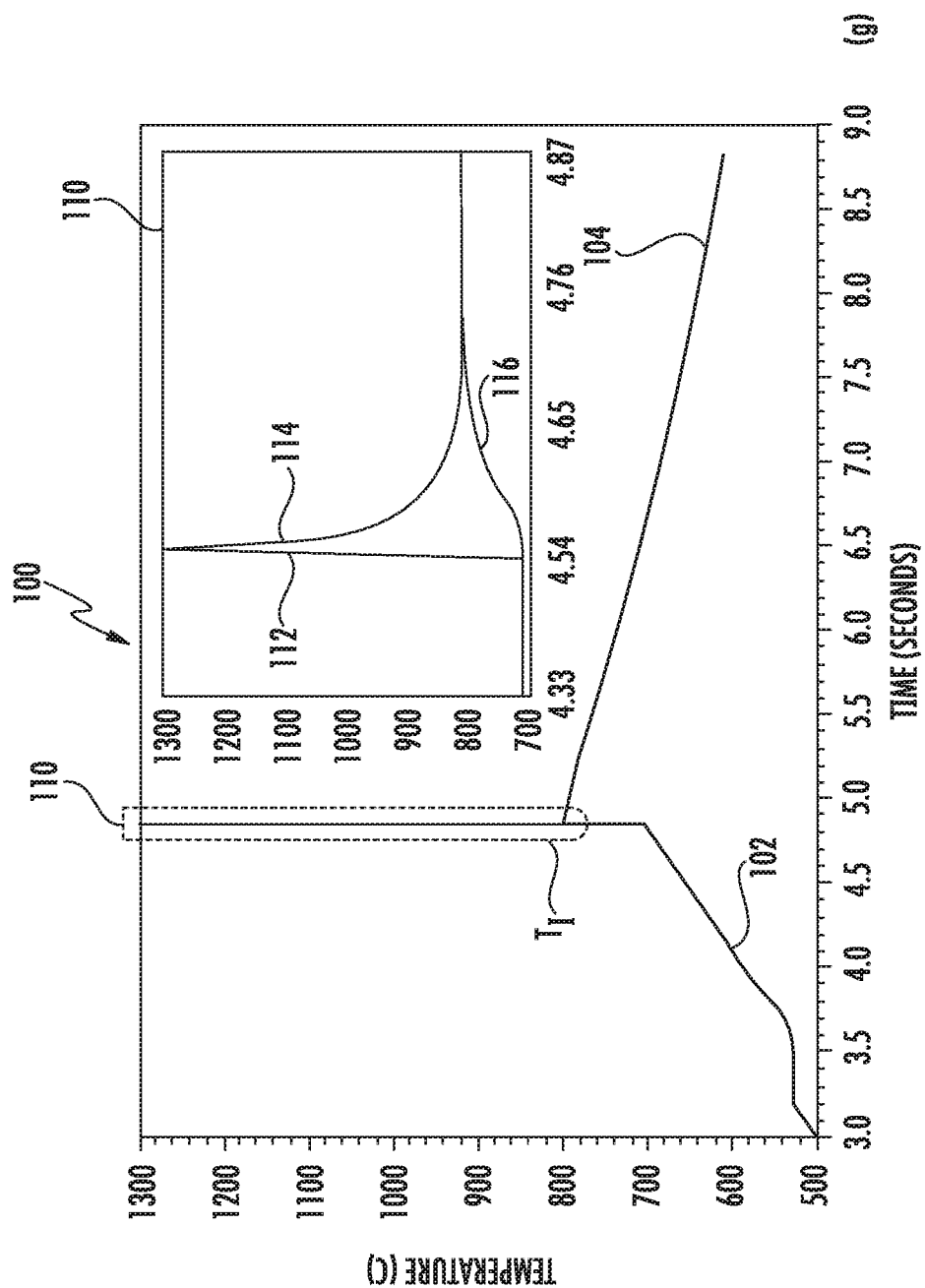
FIG. 1 depicts an example millisecond anneal heating profile according to example embodiments of the present disclosure.

Reference now will be made in detail to embodiments, one or more examples of which are illustrated in the drawings. Each example is provided by way of explanation of the embodiments, not limitation of the present disclosure. In fact, it will be apparent to those skilled in the art that various modifications and variations can be made to the embodiments without departing from the scope or spirit of the present disclosure. For instance, features illustrated or described as part of one embodiment can be used with another embodiment to yield a still further embodiment.

Thus, it is intended that aspects of the present disclosure cover such modifications and variations.

Overview

Example aspects of the present disclosure are directed to detecting substrate breakage (e.g., wafer breakage) during thermal processing. Aspects of the present disclosure are discussed with reference to a "wafer" or semiconductor wafer for purposes of illustration and discussion. Those of ordinary skill in the art, using the disclosures provided herein, will understand that the example aspects of the present disclosure can be used in association with any semiconductor substrate or other suitable substrate. In addition, the use of the term "about" in conjunction with a numerical value is intended to refer to within 10% of the stated numerical value.

In addition, aspects of the present disclosure are discussed with reference to a millisecond anneal system for purposes of illustration and discussion. Those of ordinary skill in the art, using the disclosures provided herein, will understand that example aspects of the present disclosure can be used with other suitable thermal processing systems.

Certain example aspects of the present disclosure are directed to real-time or near real-time detection of wafer breakage in a millisecond anneal system. Millisecond or ultra-fast anneal of semiconductor wafers can be achieved using an intense and brief exposure of light to heat the entire top surface of the wafer at rates that can exceed $10^4$ degrees per second. The rapid heating of the wafer surface produces a large temperature gradient through the thickness of the wafer that results in significant thermal stresses. These stresses can begin to induce strain in the wafer that bows or deforms the wafer. In some cases, the strain can result in a stress that fractures or breaks the wafer.

In other cases, the strain can continue to deform the wafer well after the application of surface heating. This continued strain can be due to fact that the surface of the wafer is heated over a time interval that is typically much shorter than a time interval needed for the wafer to reach a thermal equilibrium where the thermal strain can be potentially relieved. Subsequently, the continued strain can induce a stress that acts as an impulsive force that causes the wafer to vibrate if there is no mechanism in place to confine or restrict the wafer motion. These subsequent wafer vibrations can increase the risk of the wafer fracture, or breakage. For instance, the wafer vibrations can increase the likelihood the wafer will impact structures intended to support the wafer or restrict its motion. The vibrations can strain the wafer in a manner that opposes the strain induced by the thermal gradient remaining in wafer, thereby increasing the stress over that resulting from the thermal stress alone.

When a wafer break occurs, the processing chamber can become contaminated with pieces of the broken wafer. If the wafer breakage is not detected, the subsequent unprocessed wafer, or wafers, will be exposed to the contaminants rendering the unprocessed wafers to be scrapped.

Example aspects of the present disclosure can detect the breakage of a wafer in a time interval that begins after application of the millisecond anneal heating pulse and ends prior to the next wafer entering the process chamber (e.g., during wafer cooling). Subsequently during this time interval, a signal can be provided to the process control system to prevent further wafers from entering the process chamber to become contaminated with pieces from the broken wafer and/or to initiate other corrective control actions.

More particularly, the detection of a broken wafer, and subsequently a signal to the process control system to prevent further wafers from entering the process chamber, or other corrective control actions, can be achieved by detecting a pre-determined deviation of the values of estimated cooling model parameters and/or model fitting error metrics whose values are obtained from the temperature measurement data of the wafer during the wafer cool-down period. In some embodiments, the wafer temperature measurement data can be based on non-contact measurement of the radiation thermally emitted from the wafer.

One example embodiment of the present disclosure is directed to a process for breakage detection in a thermal processing system (e.g., a millisecond anneal system). The process includes accessing data indicative of a plurality of temperature measurements for a substrate. The plurality of measurements obtained during a cool down period for a substrate during a thermal process (e.g., a cool down following application of a millisecond anneal pulse). The process can include estimating one or more metrics associated with a cooling model based at least in part on the data indicative of the plurality of temperature measurements; and determining a breakage detection signal based at least in part on the one or more metrics associated with the cooling model. The breakage detection signal can be indicative of whether the substrate has broken during thermal processing.

In some embodiments, when the breakage detection signal is indicative of a non-broken substrate, the process can include processing a next substrate in the thermal processing system. In some embodiments, when the breakage detection signal is indicative of a broken substrate, the process can include performing a corrective action prior to processing a next substrate in the thermal processing system. The corrective action can include, for instance, moving a next substrate for thermal processing back to a cassette; opening a door of the thermal processing chamber; and removing one or more pieces of the broken substrate from the processing chamber.

In some embodiments, the plurality of temperature measurements can include one or more temperature measurements associated with a top surface of the substrate and/or one or more temperature measurements associated with a bottom surface of the substrate.

In some embodiments, the one or more metrics can include a cooling model parameter. In some embodiments, the one or more metrics can include a model fitting error (e.g., a root mean square error). In some embodiments, the cooling model can be based on Newton's law of cooling. In some embodiments, the cooling model parameter can include an exponential cooling constant in Newton's law of cooling.

In some embodiments, determining a breakage detection signal based at least in part on the one or more metrics associated with the cooling model can include comparing the one or more metrics to a predetermined range of metrics; and determining the breakage detection signal based at least in part on whether the one or more metrics falls within the predetermined range of metrics. In some embodiments, the predetermined range of metrics can include a range of metrics associated with a non-broken substrate. In some embodiments, the predetermined range of metrics can include a range of metrics associated with a broken substrate.

In some embodiments, determining a breakage detection signal based at least in part on the one or more metrics associated with the cooling model can include dividing the data indicative of a plurality of temperature measurements into a plurality of sets, each set associated with a predetermined time interval; determining one or more metrics associated with the cooling model for each set; determining at least one value associated with the one or more metrics determined for each set; comparing the value to a predetermined range of values; and determining the breakage detection signal based at least in part on whether the at least on value falls within the predetermined range of values. In some embodiments, the value is determined based at least in part on a mean or standard deviation of the one or more metrics determined for each set.

Another example embodiment of the present disclosure is directed to a temperature measurement system. The temperature measurement system can include a first temperature sensor configured to obtain temperature measurements associated with a top surface of a semiconductor substrate in a millisecond anneal system. The system can include a second temperature sensor configured to obtain temperature measurements associated with a bottom surface of a semiconductor substrate in a millisecond anneal system. The system can include at least one processing circuit configured to perform operations. The operations can include: accessing data indicative of temperature measurements obtained from the first temperature sensor and the second temperature sensor during a cool down period following application of a millisecond anneal pulse to the semiconductor substrate; estimating one or more metrics associated with a cooling model based at least in part on the data indicative of the plurality of temperature measurements; and determining a breakage detection signal based at least in part on the one or more metrics associated with the cooling model. The breakage detection signal can be indicative of whether the semiconductor substrate has broken during thermal processing. In some embodiments, the first temperature sensor and the second temperature sensor can be configured to measure temperature by measuring radiation from the semiconductor substrate. In some embodiments, the one or more metrics can include a cooling model parameter (e.g., an exponential cooling constant in Newton's law of cooling) or a model fitting error.

Another example embodiment of the present disclosure is directed to A millisecond anneal system. The system can include a processing chamber. The system can include a wafer plane plate configured to support a semiconductor substrate. The wafer plane plate dividing the processing chamber into a top chamber and a bottom chamber. The system can include one or more heat sources configured to provide a millisecond anneal pulse to a top surface of the semiconductor substrate. The system can include a first temperature sensor configured to obtain temperature measurements associated the top surface of semiconductor substrate. The system can include a second temperature sensor configured to obtain temperature measurements associated with the bottom surface of the semiconductor substrate. The system can include at least one processing circuit configured to perform operations. The operations can include: accessing data indicative of temperature measurements obtained from the first temperature sensor and the second temperature sensor during a cool down period following application of the millisecond anneal pulse to the semiconductor substrate; estimating one or more metrics associated with a cooling model based at least in part on the data indicative of the plurality of temperature measurements; and determining a breakage detection signal based at least in part on the one or more metrics associated with the cooling model. The breakage detection signal indicative of whether the semiconductor substrate has broken during thermal processing.

Example Millisecond Anneal Systems

An example millisecond anneal system can be configured to provide an intense and brief exposure of light to heat the top surface of a wafer at rates that can exceed, for instance, about $10^{4°}$ C./s. FIG. 1 depicts an example temperature profile 100 of a semiconductor substrate achieved using a millisecond anneal system. As shown in FIG. 1, the bulk of the semiconductor substrate (e.g., a silicon wafer) is heated to an intermediate temperature $T_i$ during a ramp phase 102. The intermediate temperature can be in the range of about 450° C. to about 900° C. When the intermediate temperature $T_i$ is reached, the top side of the semiconductor substrate can be exposed to a very short, intense flash of light resulting in heating rates of up to about $10^{4°}$ C./s. Window 110 illustrates the temperature profile of the semiconductor substrate during the short, intense flash of light. Curve 112 represents the rapid heating of the top surface of the semiconductor substrate during the flash exposure. Curve 116 depicts the temperature of the remainder or bulk of the semiconductor substrate during the flash exposure. Curve 114 represents the rapid cool down by conductive of cooling of the top surface of the semiconductor substrate by the bulk of the semiconductor substrate acting as a heat sink. The bulk of the semiconductor substrate acts as a heat sink generating high top side cooling rates for the substrate. Curve 104 represents the slow cool down of the bulk of the semiconductor substrate by thermal radiation and convection, with a process gas as a cooling agent.

An example millisecond anneal system can include a plurality of arc lamps (e.g., four Argon arc lamps) as light sources for intense millisecond long exposure of the top surface of the semiconductor substrate—the so called "flash." The flash can be applied to the semiconductor substrate when the substrate has been heated to an intermediate temperature (e.g., about 450° C. to about 900° C.). A plurality of continuous mode arc lamps (e.g., two Argon arc lamps) can be used to heat the semiconductor substrate to the intermediate temperature. In some embodiments, the heating of the semiconductor substrate to the intermediate temperature is accomplished through the bottom surface of the semiconductor substrate at a ramp rate which heats the entire bulk of the wafer.

Figure 2:
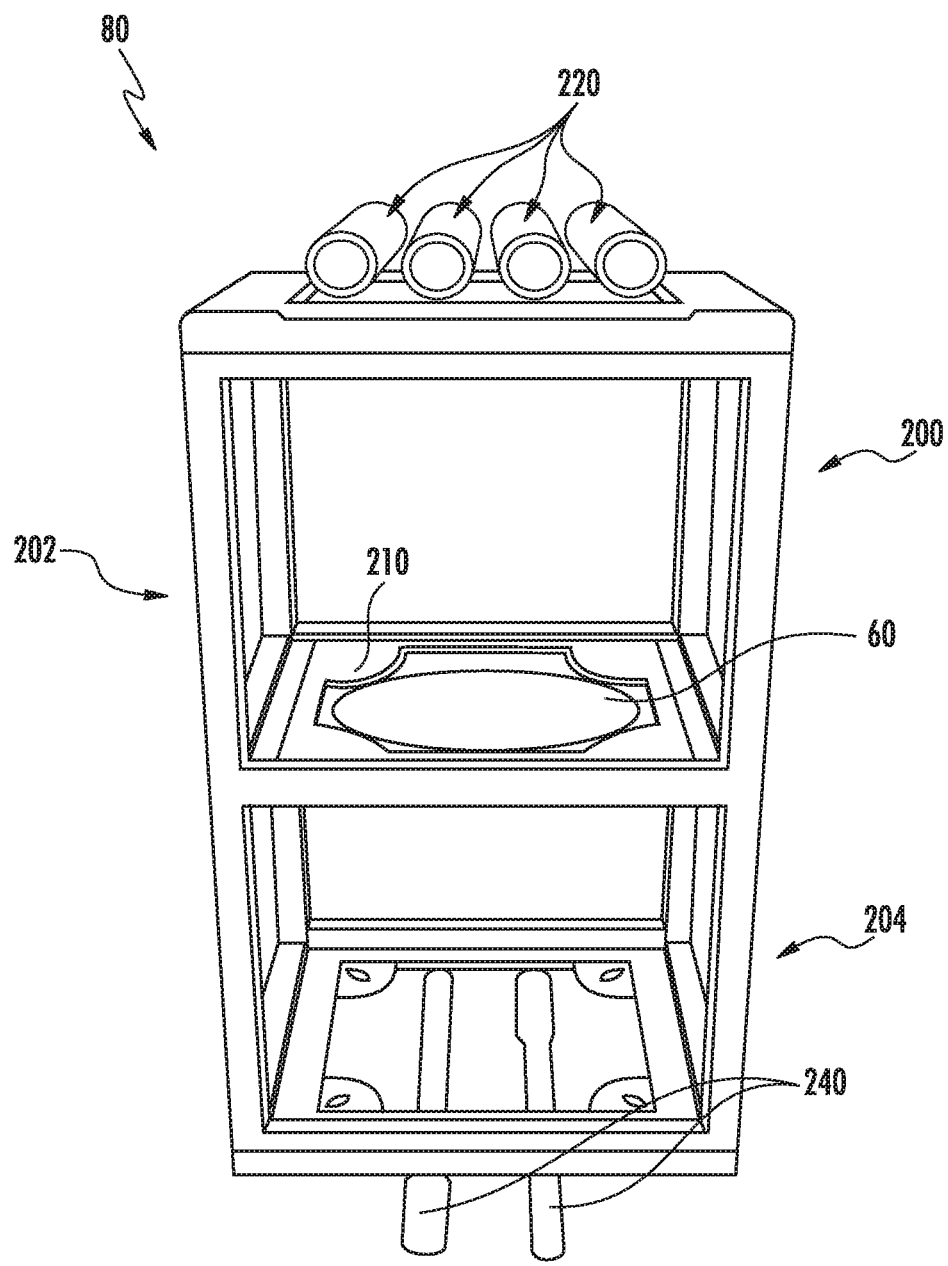
FIG. 2 depicts an example perspective view of a portion of an example millisecond anneal system according to example embodiments of the present disclosure.
Figure 3:
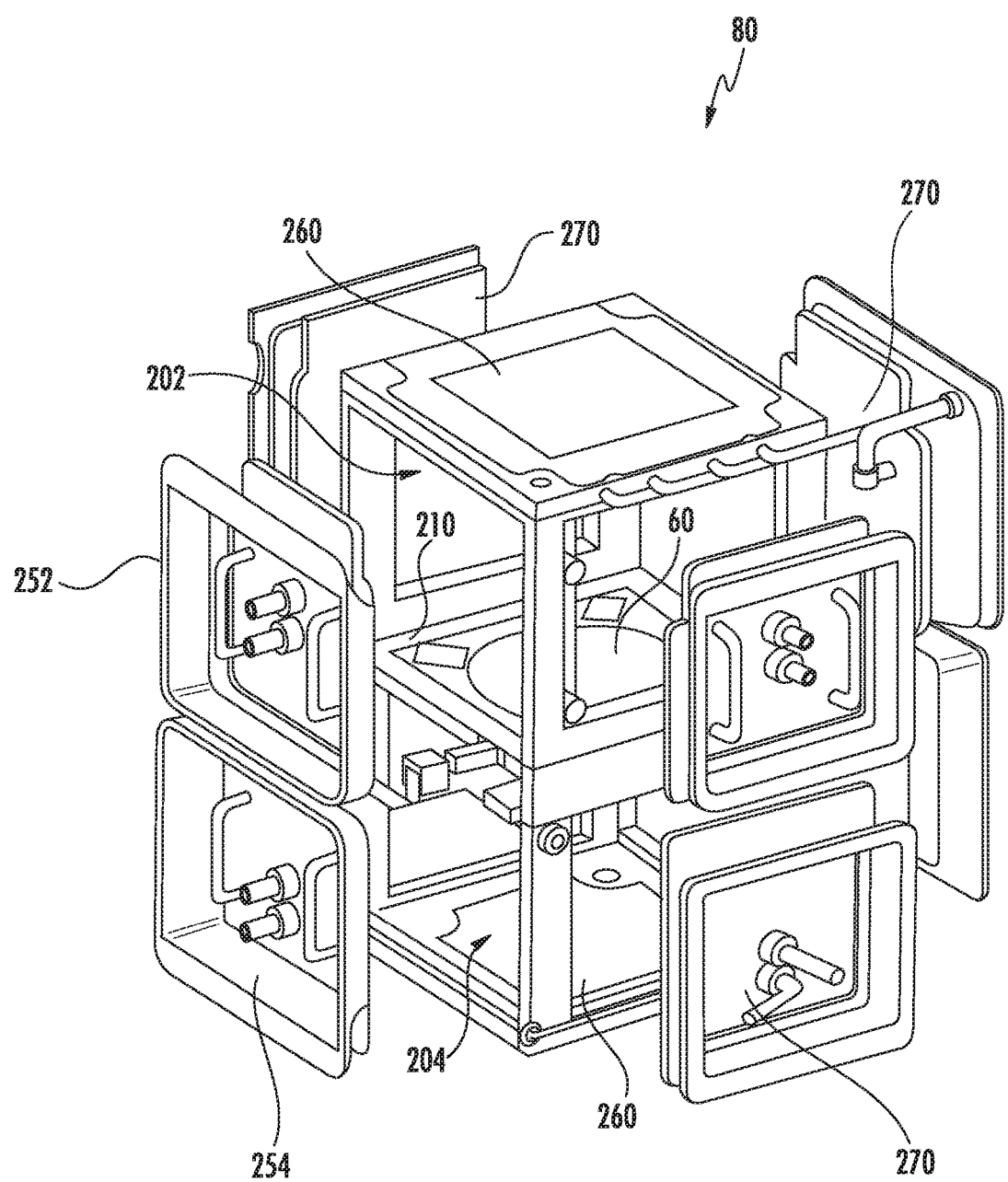
FIG. 3 depicts an exploded view of an example millisecond anneal system according to example embodiments of the present disclosure.
Figure 4:
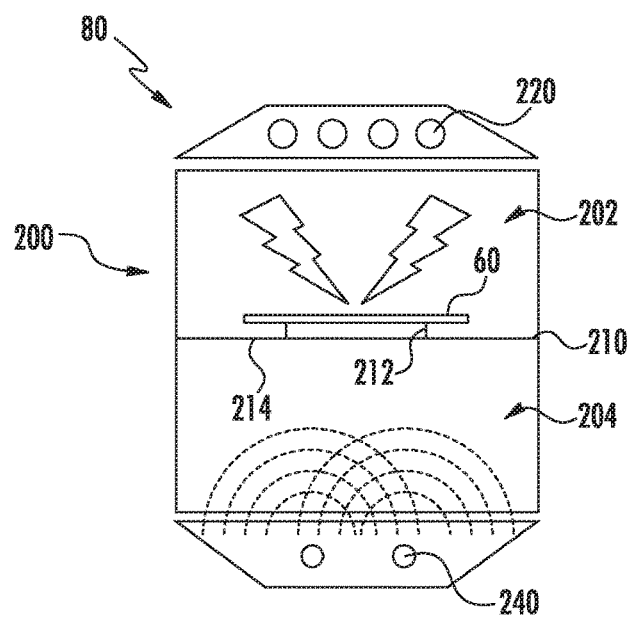
FIG. 4 depicts a cross-sectional view of an example millisecond anneal system according to example embodiments of the present disclosure.

FIGS. 2 to 5 depict various aspects of an example millisecond anneal system 80 according to example embodiments of the present disclosure. As shown in FIGS. 2-4, a millisecond anneal system 80 can include a process chamber 200. The process chamber 200 can be divided by a wafer plane plate 210 into a top chamber 202 and a bottom chamber 204. A semiconductor substrate 60 (e.g., a silicon wafer) can be supported by support pins 212 (e.g., quartz support pins) mounted to a wafer support plate 214 (e.g., quartz glass plate inserted into the wafer plane plate 210).

As shown in FIGS. 2 and 4, the millisecond anneal system 80 can include a plurality of arc lamps 220 (e.g., four Argon arc lamps) arranged proximate the top chamber 202 as light sources for intense millisecond long exposure of the top surface of the semiconductor substrate 60—the so called "flash." The flash can be applied to the semiconductor substrate when the substrate has been heated to an intermediate temperature (e.g., about 450° C. to about 900° C.).

A plurality of continuous mode arc lamps 240 (e.g., two Argon arc lamps) located proximate the bottom chamber 204 can be used to heat the semiconductor substrate 60 to the intermediate temperature. In some embodiments, the heating of the semiconductor substrate 60 to the intermediate temperature is accomplished from the bottom chamber 204 through the bottom surface of the semiconductor substrate at a ramp rate which heats the entire bulk of the semiconductor substrate 60.

As shown in FIG. 3, the light to heat the semiconductor substrate 60 from the bottom arc lamps 240 (e.g., for use in heating the semiconductor substrate to an intermediate temperature) and from the top arc lamps 220 (e.g., for use in providing millisecond heating by flash) can enter the processing chamber 200 through water windows 260 (e.g., water cooled quartz glass windows). In some embodiments, the water windows 260 can include a sandwich of two quartz glass panes between which an about a 4 mm thick layer of water is circulating to cool the quartz panes and to provide an optical filter for wavelengths, for instance, above about 1400 nm.

Figure 5:
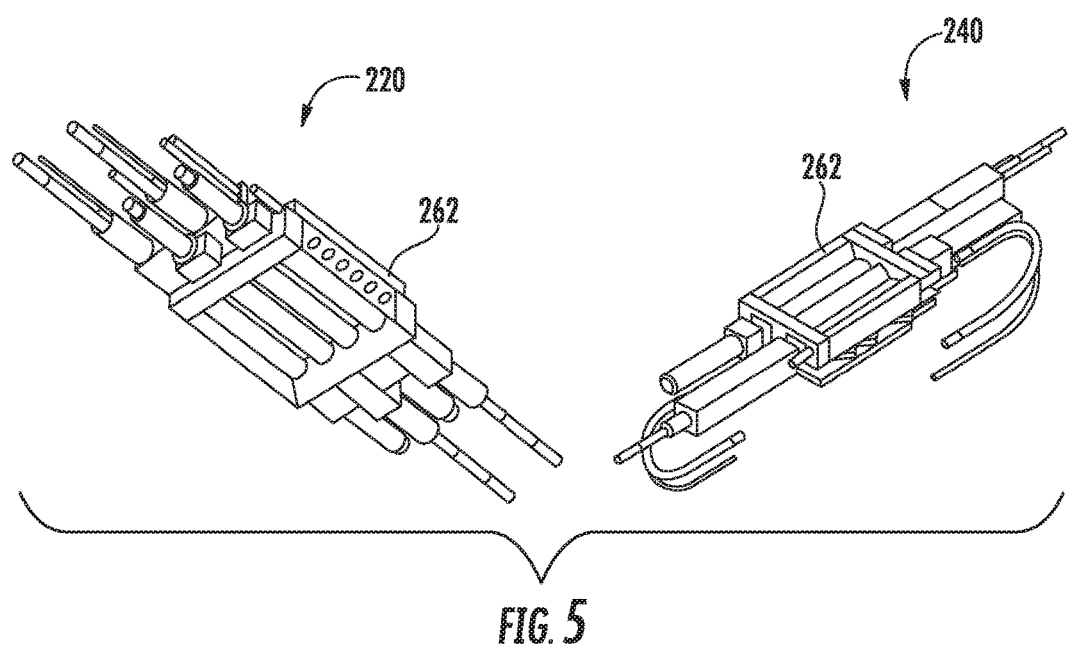
FIG. 5 depicts a perspective view of example lamps used in a millisecond anneal system according to example embodiments of the present disclosure.

As further illustrated in FIG. 3, process chamber walls 250 can include reflective mirrors 270 for reflecting the heating light. The reflective mirrors 270 can be, for instance, water cooled, polished aluminum panels. In some embodiments, the main body of the arc lamps used in the millisecond anneal system can include reflectors for lamp radiation. For instance, FIG. 5 depicts a perspective view of both a top lamp array 220 and a bottom lamp array 240 that can be used in the millisecond anneal system 200. As shown, the main body of each lamp array 220 and 240 can include a reflector 262 for reflecting the heating light. These reflectors 262 can form a part of the reflecting surfaces of the process chamber 200 of the millisecond anneal system 80.

The temperature uniformity of the semiconductor substrate can be controlled by manipulating the light density falling onto different regions of the semiconductor substrate. In some embodiments, uniformity tuning can be accomplished by altering the reflection grade of small size reflectors to the main reflectors and/or by use of edge reflectors mounted on the wafer support plane surrounding the wafer.

Figure 6:
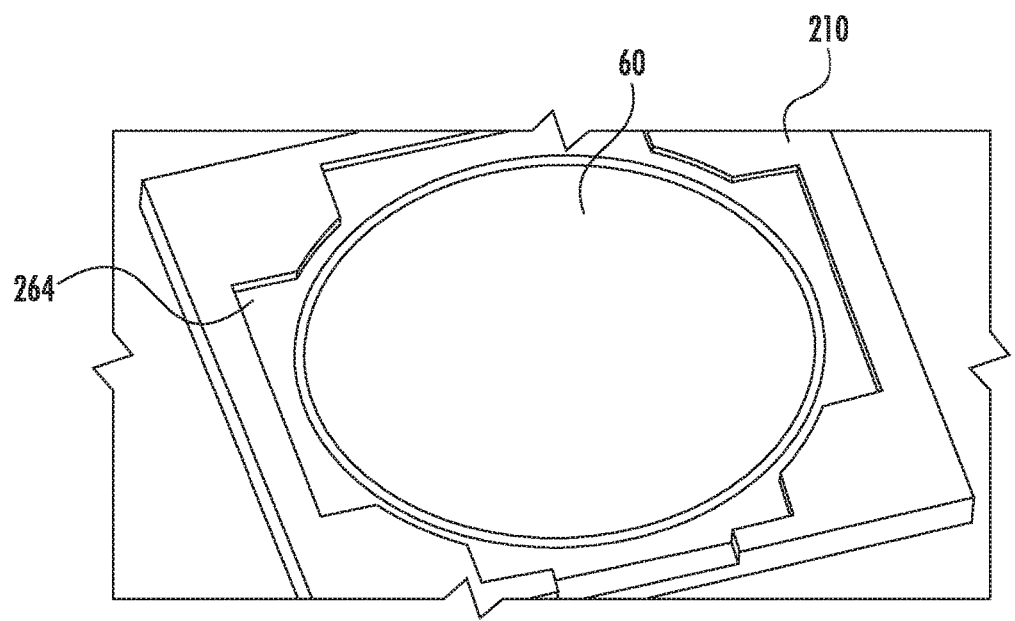
FIG. 6 depicts example edge reflectors used in a wafer plane plate of a millisecond anneal system according to example embodiments of the present disclosure.

For instance, edge reflectors can be used to redirect light from the bottom lamps 240 to an edge of the semiconductor substrate 60. As an example, FIG. 6 depicts example edge reflectors 264 that form a part of the wafer plane plate 210 that can be used to direct light from the bottom lamps 240 to the edge of the semiconductor substrate 60. The edge reflectors 264 can be mounted to the wafer plane plate 210 and can surround or at least partially surround the semiconductor substrate 60.

Figure 7:
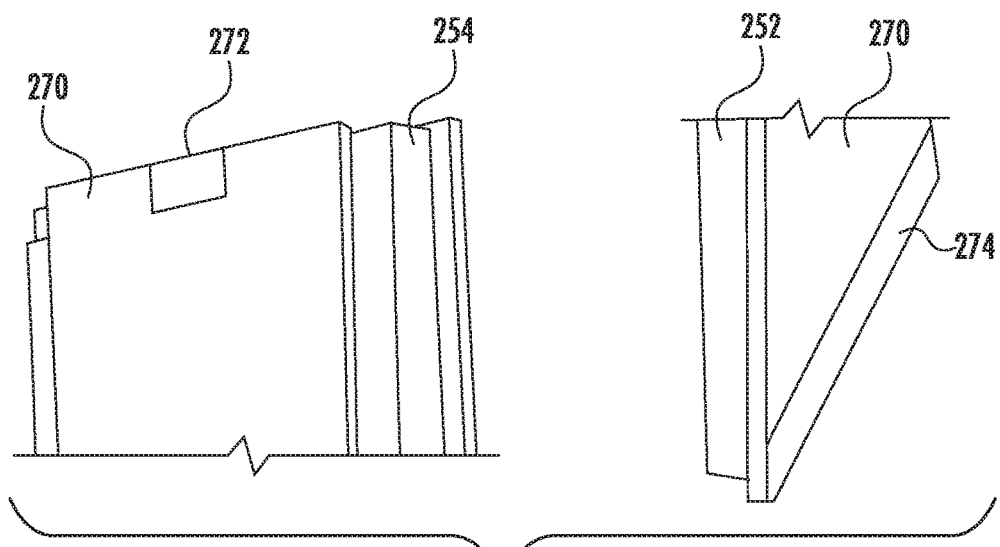
FIG. 7 depicts example reflectors that can be used in a millisecond anneal system according to example embodiments of the present disclosure.

In some embodiments, additional reflectors can also be mounted on chamber walls near the wafer plane plate 210. For example, FIG. 7 depicts example reflectors that can be mounted to the process chamber walls that can act as reflector mirrors for the heating light. More particularly, FIG. 7 shows an example wedge reflector 272 mounted to lower chamber wall 254. FIG. 7 also illustrates a reflective element 274 mounted to reflector 270 of an upper chamber wall 252. Uniformity of processing of the semiconductor substrate 60 can be tuned by changing the reflection grade of the wedge reflectors 272 and/or other reflective elements (e.g., reflective element 274) in the processing chamber 200.

Figure 8:
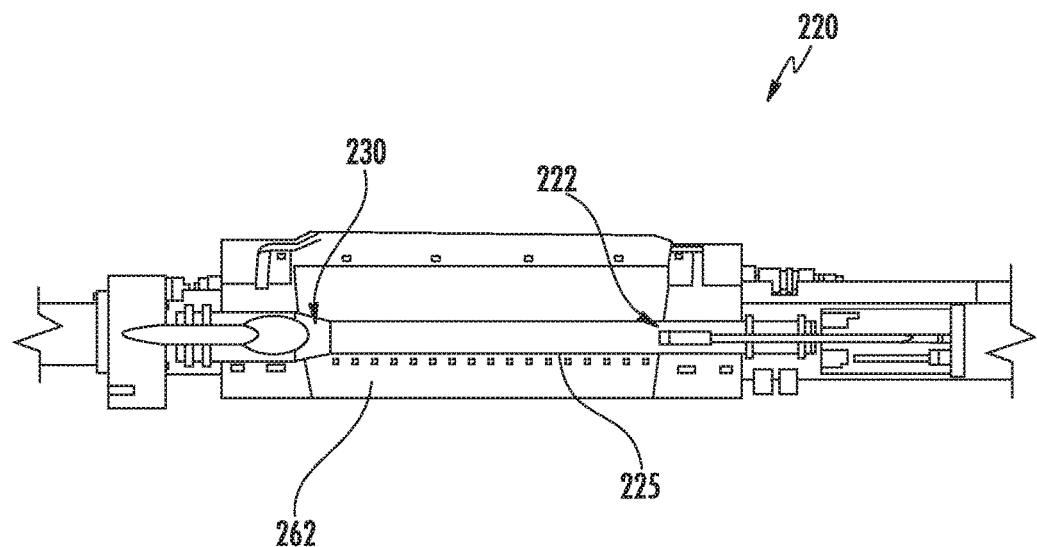
FIG. 8 depicts an example arc lamp that can be used in a millisecond anneal system according to example embodiments of the present disclosure.

FIGS. 8-11 depict aspects of example upper arc lamps 220 that can be used as light sources for intense millisecond long exposure of the top surface of the semiconductor substrate 60 (e.g., the "flash"). For instance, FIG. 8 depicts a cross-sectional view of an example arc lamp 220. The arc lamp 220 can be, for instance, an open flow arc lamp, where pressurized Argon gas (or other suitable gas) is converted into a high pressure plasma during an arc discharge. The arc discharge takes place in a quartz tube 225 between a negatively charged cathode 222 and a spaced apart positively charged anode 230 (e.g., spaced about 300 mm apart).

Figure 9:
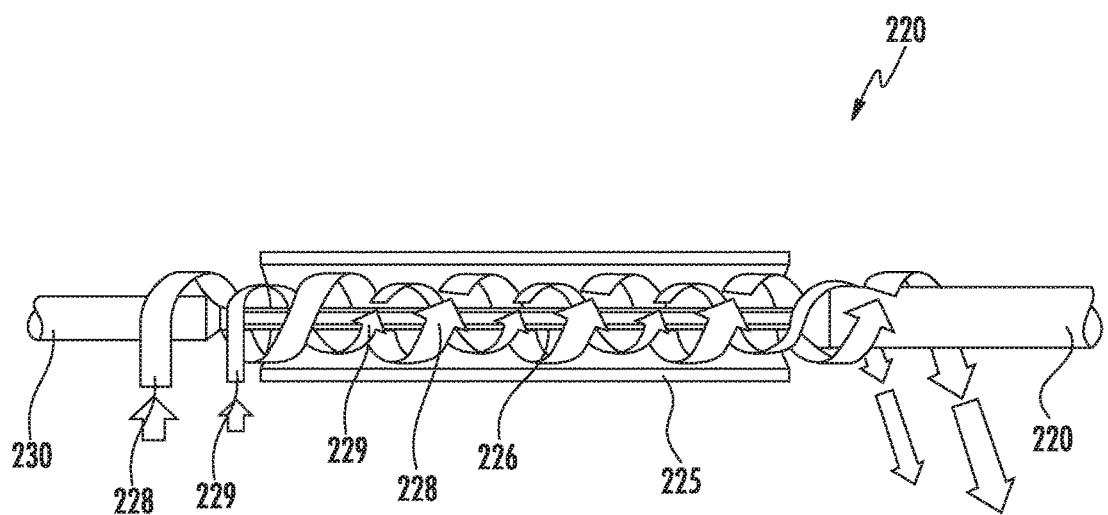
FIGS. 9-10 depict the operation of an example arc lamp according to example embodiments of the present disclosure.

As soon as the voltage between the cathode 222 and the anode 230 reaches a breakdown voltage of Argon (e.g., about 30 kV) or other suitable gas, a stable, low inductive plasma is formed which emits light in the visible and UV range of the electromagnetic spectrum. As shown in FIG. 9, the lamp can include a lamp reflector 262 that can be used to reflect light provided by the lamp for processing of the semiconductor substrate 60.

Figure 10:
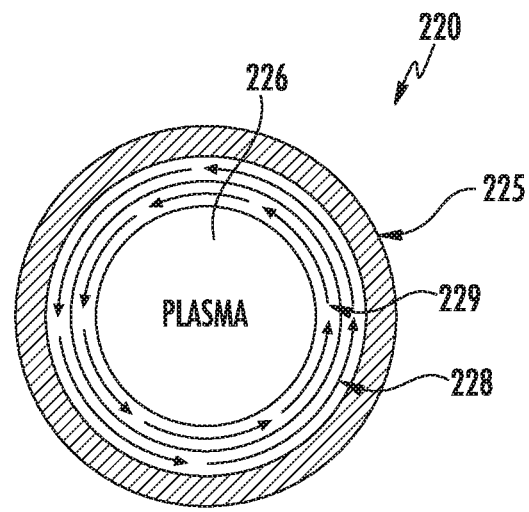
Figure 11:
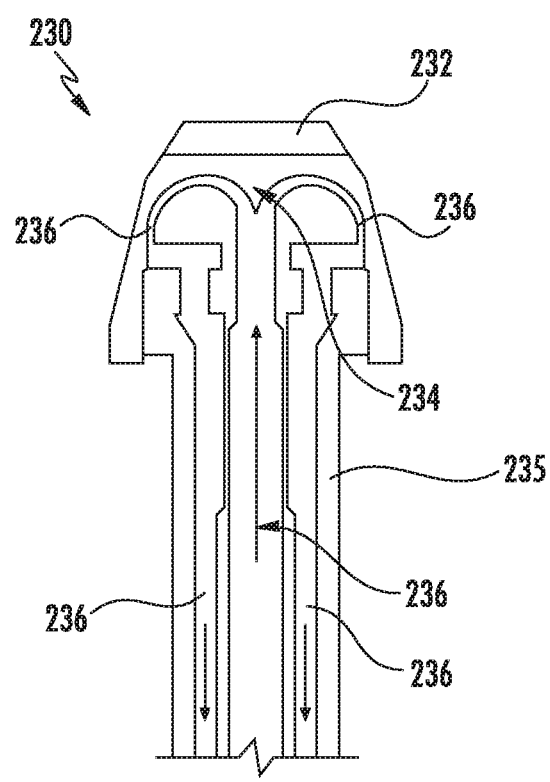
FIG. 11 depicts a cross-sectional view of an example electrode according to example embodiments of the present disclosure.

FIGS. 10 and 11 depict aspects of example operation of an arc lamp 220 in millisecond anneal system 80 according to example embodiments of the present disclosure. More particularly, a plasma 226 is contained within a quartz tube 225 which is water cooled from the inside by a water wall 228. The water wall 228 is injected at high flow rates on the cathode end of the lamp 200 and exhausted at the anode end. The same is true for the Argon gas 229, which is also entering the lamp 220 at the cathode end and exhausted from the anode end. The water forming the water wall 228 is injected perpendicular to the lamp axis such that the centrifugal action generates a water vortex. Hence, along the center line of the lamp a channel is formed for the Argon gas 229. The Argon gas column 229 is rotating in the same direction as the water wall 228. Once a plasma 226 has formed, the water wall 228 is protecting the quartz tube 225 and confining the plasma 226 to the center axis. Only the water wall 228 and the electrodes (cathode 230 and anode 222) are in direct contact with the high energy plasma 226.

FIG. 11 depicts a cross sectional view of an example electrode (e.g., cathode 230) used in conjunction with an arc lamp according to example embodiments of the present disclosure. FIG. 11 depicts a cathode 230. However, a similar construction can be used for the anode 222.

In some embodiments, as the electrodes experience a high heat load, one or more of the electrodes can each include a tip 232. The tip can be made from tungsten. The tip can be coupled to and/or fused to a water cooled copper heat sink 234. The copper heat sink 234 can include at least a portion the internal cooling system of the electrodes (e.g., one or more water cooling channels 236. The electrodes can further include a brass base 235 with water cooling channels 236 to provide for the circulation of water or other fluid and the cooling of the electrodes.

The arc lamps used in example millisecond anneal systems according to aspects of the present disclosure can be an open flow system for water and Argon gas. However, for conservation reasons, both media can be circulated in a close loop system in some embodiments.

Figure 12:
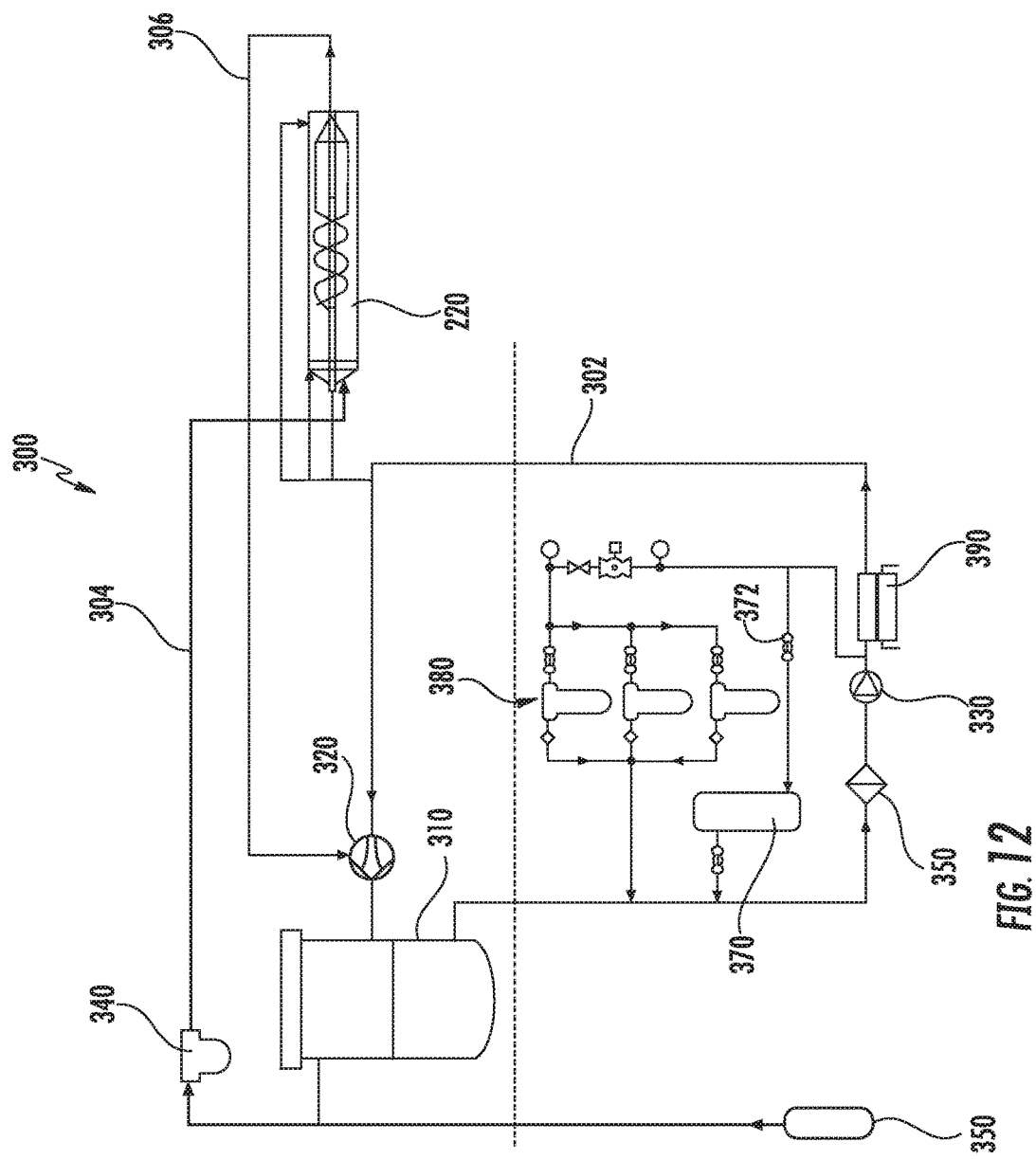
FIG. 12 depicts an example closed loop system for supplying water and gas (e.g., Argon gas) to example arc lamps used in a millisecond anneal system according to example embodiments of the present disclosure.

FIG. 12 depicts an example closed loop system 300 for supplying water and Argon gas needed to operate the open flow Argon arc lamps used in millisecond anneal systems according to example embodiments of the present disclosure.

More particularly, high purity water 302 and Argon 304 is fed to the lamp 220. The high purity water 302 is used for the water wall and the cooling of the electrodes. Leaving the lamp is a gas/water mixture 306. This water/gas mixture 306 is separated into gas free water 302 and dry Argon 304 by separator 310 before it can be re-fed to the inlets of the lamp 220. To generate the required pressure drop across the lamp 220, the gas/water mixture 306 is pumped by means of a water driven jet pump 320.

A high power electric pump 330 supplies the water pressure to drive the water wall in the lamp 220, the cooling water for the lamp electrodes, and the motive flow for the jet pump 320. The separator 310 downstream to the jet pump 320 can be used extracting the liquid and the gaseous phase from the mixture (Argon). Argon is further dried in a coalescing filter 340 before it re-enters the lam 220. Additional Argon can be supplied from Argon source 350 if needed.

The water is passing through one or more particle filters 350 to remove particles sputtered into the water by the arc. Ionic contaminations are removed by ion exchange resins. A portion of water is run through mixed bed ion exchange filters 370. The inlet valve 372 to the ion exchange bypass 370 can be controlled by the water resistivity. If the water resistivity drops below a lower value the valve 372 is opened, when it reaches an upper value the valve 372 is closed. The system can contain an activated carbon filter bypass loop 380 where a portion of the water can be additionally filtered to remove organic contaminations. To maintain the water temperature, the water can pass through a heat exchanger 390.

Figure 13:
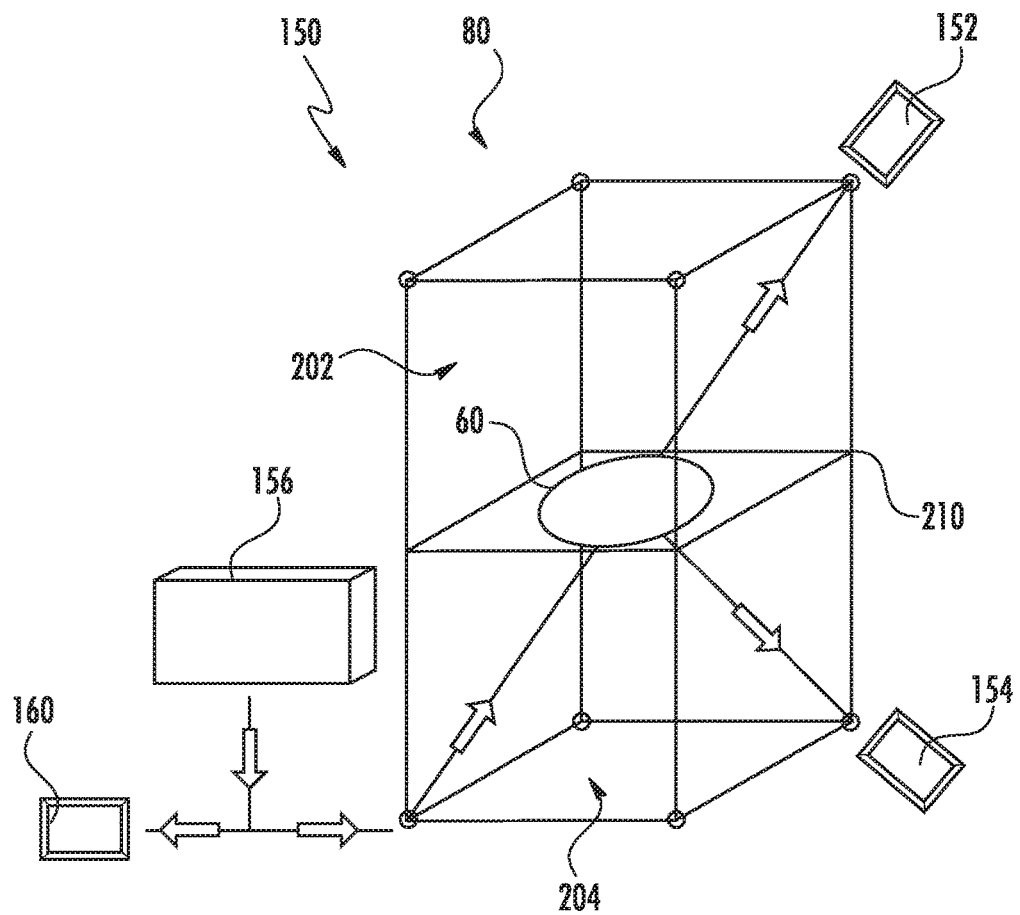
FIG. 13 depicts an example temperature measurement system for a millisecond anneal system according to example embodiments of the present disclosure.

Millisecond anneal systems according to example embodiments of the present disclosure can include the ability to independently measure temperature of both surfaces (e.g., the top and bottom surfaces) of the semiconductor substrate. FIG. 13 depicts an example temperature measurement system 150 for millisecond anneal system 200.

A simplified representation of the millisecond anneal system 200 is shown in FIG. 13. The temperature of both sides of a semiconductor substrate 60 can be measured independently by temperature sensors, such as temperature sensor 152 and temperature sensor 154. Temperature sensor 152 can measure a temperature of a top surface of the semiconductor substrate 60. Temperature sensor 154 can measure a bottom surface of the semiconductor substrate 60. In some embodiments, narrow band pyrometric sensors with a measurement wavelength of about 1400 nm can be used as temperature sensors 152 and/or 154 to measure the temperature of, for instance, a center region of the semiconductor substrate 60. In some embodiments, the temperature sensors 152 and 154 can be ultra-fast radiometers (UFR) that have a sampling rate that is high enough to resolve the millisecond temperature spike cause by the flash heating.

The readings of the temperature sensors 152 and 154 can be emissivity compensated. As shown in FIG. 13, the emissivity compensation scheme can include a diagnostic flash 156, a reference temperature sensor 158, and the temperature sensors 152 and 154 configured to measure the top and bottom surface of the semiconductor wafers. Diagnostic heating and measurements can be used with the diagnostic flash 156 (e.g., a test flash). Measurements from reference temperature sensor 158 can be used for emissivity compensation of temperature sensors 152 and 154

In some embodiments, the millisecond anneal system 200 can include water windows. The water windows can provide an optical filter that suppresses lamp radiation in the measurement band of the temperature sensors 152 and 154 so that the temperature sensors 152 and 154 only measure radiation from the semiconductor substrate.

The readings of the temperature sensors 152 and 154 can be provided to a processor circuit 160. The processor circuit 10 can be located within a housing of the millisecond anneal system 200, although alternatively, the processor circuit 160 may be located remotely from the millisecond anneal system 200. The various functions described herein may be performed by a single processor circuit if desired, or by other combinations of local and/or remote processor circuits.

Figure 14:
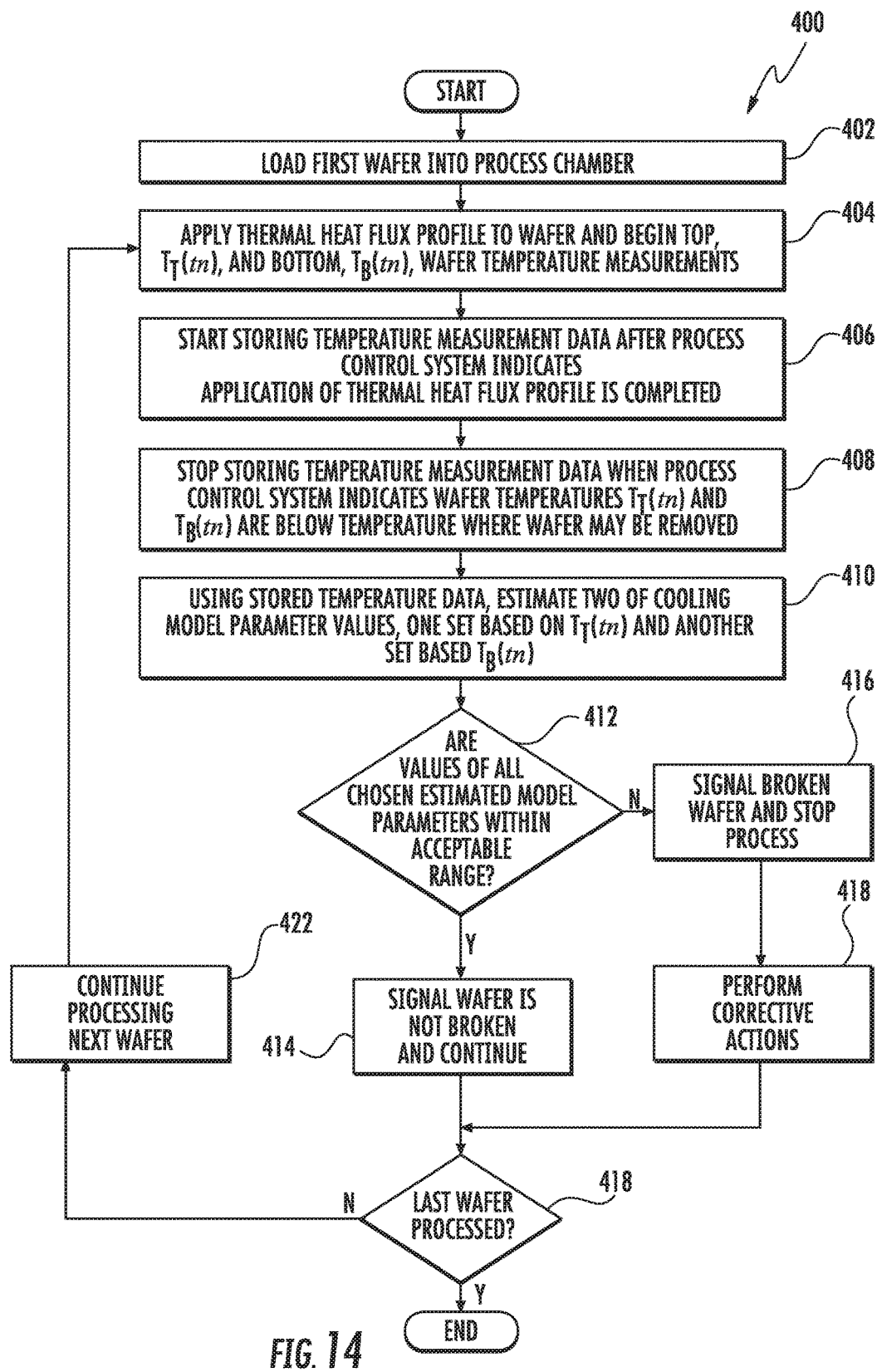
FIG. 14 depicts a flow diagram of an example process for wafer breakage detection according to example embodiments of the present disclosure.
Figure 15:
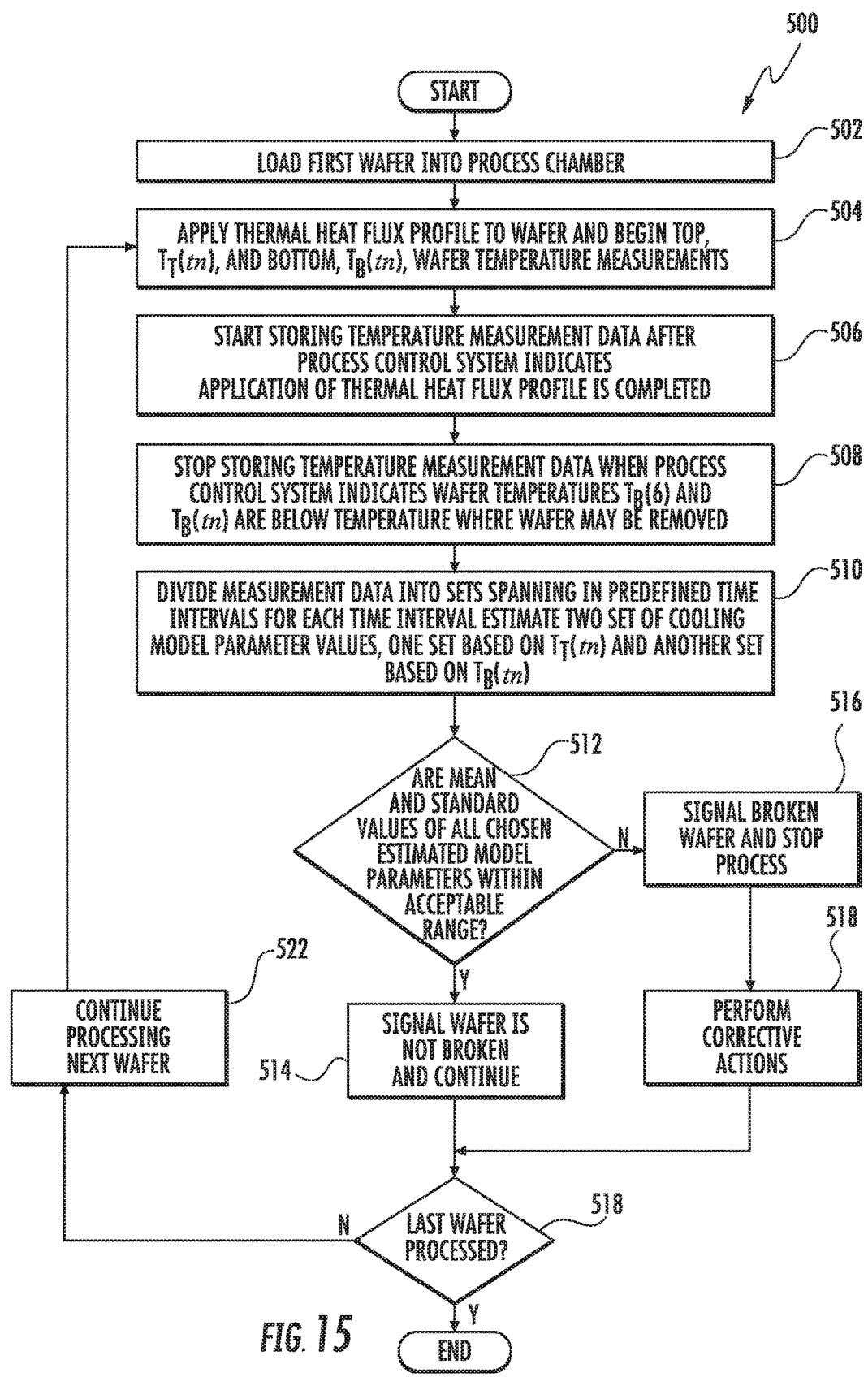
FIG. 15 depicts a flow diagram of an example process for wafer breakage detection according to example embodiments of the present disclosure.

In some embodiments, the processor circuit 160 can be configured to execute computer-readable instructions stored in one or more memory devices to execute control routines described herein, such as any of the control routines for determining wafer or semiconductor substrate breakage set forth in FIGS. 14 and 15. In some embodiments, the wafer breakage detection processes according to example aspects of the present disclosure can be implemented using the temperature measurement and control system described in U.S. Pat. No. 7,616,872, which is incorporated by referenced herein.

Example Wafer Breakage Detection

According to example aspects of the present disclosure, wafer breakage detection can be achieved by detecting a pre-determined deviation of the values of estimated cooling model parameters and/or model fitting error metrics whose values are obtained from the temperature measurement data of the wafer during the wafer cool-down period (e.g., the time period corresponding to curve 104 of FIG. 1). In some embodiments, the wafer temperature measurement data can be based on non-contact measurement of the radiation thermally emitted from the wafer (e.g., non-contact measurements obtained by sensors 152 and 154 of FIG. 13).

In some embodiments, a wafer breakage detection process can begin by measuring the temperature of the top and/or bottom of the wafer using the radiation thermally emitted from the wafer during the wafer cool-down period (e.g., the time period corresponding to curve 104 of FIG. 1). The wafer cool down period can start immediately after the end of the application of the millisecond anneal heating pulse. Once obtained, the cool-down temperature measurement data can be fit to a defined cooling model. The cooling model can be, for instance, based on, for example, Newton's law of cooling. This fitting can include estimating one or more parameters of the model that provide the best fit of the measured temperature data to the cooling model. At least one of the parameters can be, for instance, the exponential cooling constant parameter in Newton's law of cooling model (also referred to as the heat transfer coefficient). In some embodiments, the best fit can be defined in the least squared error sense (e.g., using any suitable regression analysis).

Once established, data indicative of the model parameters and/or model fitting errors can serve as metrics that are used to detect when a wafer or other semiconductor substrate is broken. More particularly, a range of values of the metrics (e.g., model parameters and/or model fitting errors) for broken wafers can be pre-determined using the model. This range of values of metrics can be distinctly different from the range of values of metrics (e.g., model parameters and/or model fitting errors) associated with unbroken wafers.

The detection of a broken wafer can be made in real time or near-real time based on measured temperature data by determining if the values of the chosen metrics determined based on the measured temperature data fall within the pre-defined range of values associated with broken wafers. Finally, after detecting a broken wafer, a signal can be provided, for instance, to a process control system to prevent further wafers from entering the process chamber to become contaminated with pieces from the broken wafer or to initiate other corrective control actions.

An advantage in using the value of metrics from a cooling mode (e.g., model parameters and/or model fitting errors) to detect broken wafers is that the value of particular model parameters will not be very sensitive to changes in the heat flux profiles applied to the wafer since the model is based on the physical process of cooling that occurs under specific, and the relatively constant, physical configurations and bulk properties of both the wafer and the surrounding ambient.

For example, Newton's law of cooing is based on a number of assumptions, such as, that the rate of heat conduction in the wafer is much larger than the rate of heat loss by conduction or convection of the wafer. Another assumption can be that the wafer is "thermally thin" such that the temperature of the object is approximately equal throughout its volume. Another assumption can be that the rate of heat loss is not dependent on the temperature differential between, for example the wafer and the ambient environment. These assumptions do not depend on the applied heat flux profile applied to the wafer but only on the physical configuration and bulk properties of the wafer and ambient. As a result, for any particular model, the conditions where the assumptions are strongly satisfied will allow the model to provide accurate predictions. In particular when a wafer does not break, these assumptions, for example as stated previously for Newton's law of cooling, can be strongly satisfied, except for the heat transfer rate into the ambient gas which has a weak dependence on the absolute temperature of the surround ambient gas in the cooling interval.

Given that the cooling model can be dependent on the physical process of cooling that occurs under specific, and relatively constant physical configurations and/or bulk properties of both the wafer and the surrounding ambient, detecting a wafer break can be more reliable by virtue that a broken wafer will not satisfy all these assumptions. For example, when a wafer breaks, either into many small pieces or into two large pieces, the wafer will be in a different physical configuration as compared to the physical configuration of a non-broken wafer. As a result, for example, the exponential cooling constant in Newton's law of cooling for a broken wafer will be different from that of a non-broken wafer.

In addition, the wafer breakage event can be a random event in terms of the number of fractured wafer pieces, their movement, and/or interval of time the wafer pieces come to rest in their final positions. Attempting to fit the cooling model to the temperature data obtained while the wafer was breaking violates all the assumptions of the model resulting in model fit that does not accurately follow the measured temperature data. Assessing how accurately the model follows the data can be made using various error measures, such as the root of the mean square error. This error metric can be less than about three degrees when the temperature data, from wafers that do not break, includes the entire cooling interval. This residual error is due to the weak dependence of the heat transfer coefficient to the temperature of the ambient gas surrounding the wafer.

In the case of a broken wafer, the error measure is typically much larger than three degrees, especially if the motion of the breaking wafer pieces continues over a large fraction, such as 10% or more, of the measurement interval used to obtain the temperature data that is used in the model fit. In the case where the motion of the broken wafer pieces stop very abruptly, for example, in an interval that is less than 1% of the measurement interval used to obtain temperature data for the model fit, the error measure may also be less than about three degrees. However, the value of the model parameter, for example, the exponential cooling constant parameter in Newton's law of cooling, will be significantly different than the value obtained when the wafer does not break. Therefore, using the values of the chosen model parameters, such as the exponential cooling constant in Newton's law of cooling, and fitting error metric, increases the reliability in correctly detecting a broken wafer.

FIG. 14 depicts a flow diagram of one example process (400) for wafer breakage detection in a millisecond anneal system according to example embodiments of the present disclosure. The process (400) can be implemented, for instance, using the millisecond anneal system 200 and temperature measurement system 150 described herein. FIG. 14 illustrates steps performed in a particular order for purposes of illustration and discussion. Those of ordinary skill in the art, using the disclosures provided herein, will understand that various steps of any of the methods disclosed herein can be adapted, modified, expanded, omitted, and/or rearranged in various ways without deviating from the scope of the present disclosure.

As shown, the process (400) can include loading a first wafer into a process chamber at (402). For instance, a semiconductor substrate 60 can be loaded into millisecond anneal system 200. At (402), the method can include applying a thermal heat flux profile to the wafer (e.g., the flash) and/or beginning to obtain temperature measurements of the top surface $T_T(t_n)$ and to obtain temperature measurements of the bottom surface $T_B(t_n)$ of the wafer, where the n discrete time instances of the measurements are denoted by $t_n$.

The process (400) can then start storing temperature measurement data a predetermined time after (e.g., 50 milliseconds) after the process control system indicates application of a thermal heat flux profile is completed as shown at (406). The process can stop storing temperature measurement data when the process control system indicates wafer temperatures $T_T(t_n)$ and $T_B(t_n)$ are below a temperature where the wafer can be removed as shown at (408).

The process (400) can then include using the stored temperature data to estimate two sets of cooling model parameter values and/or model fitting error metrics (e.g., root mean square error) (410). One set can be based on the temperature measurements of the top surface $T_T(t_n)$. Another set can be based on temperature measurements of the bottom surface $T_B(t_n)$. The cooling model parameter values can include, for instance, an exponential cooling constant in Newton's law of cooling.

The process (400) can then determine whether chosen estimated model parameters are within an acceptable range associated with a non-broken wafer (412). If so, the control system can provide a signal indicating that the wafer is not broken (414). If the estimated model parameters are not within the acceptable range, the control system can provide a signal indicating that the wafer is broken (416). The process can then include performing corrective actions (418), such as sending a signal to a process control system to prevent the next wafer from being loaded into the chamber until one or more pieces of the broken wafer are removed from the chamber.

As shown in FIG. 14, this process (400) can continue until it is determined at (420) the last wafer is processed, at which point the process ends. If the last wafer has not been processed, the process (400) can include processing the next wafer (422).

FIG. 15 depicts a flow diagram of one example process (500) for wafer breakage detection in a millisecond anneal system according to example embodiments of the present disclosure. The process (500) can be implemented, for instance, using the millisecond anneal system 200 and temperature measurement system 150 described herein. FIG. 15 illustrates steps performed in a particular order for purposes of illustration and discussion. Those of ordinary skill in the art, using the disclosures provided herein, will understand that various steps of any of the methods disclosed herein can be adapted, modified, expanded, omitted, and/or rearranged in various ways without deviating from the scope of the present disclosure.

As shown, the process (500) can include loading a first wafer into a process chamber at (502). For instance, a semiconductor substrate 60 can be loaded into millisecond anneal system 200. At (502), the method can include applying a thermal heat flux profile to the wafer and/or beginning to obtain temperature measurements of the top surface $T_T(t_n)$ and to obtain temperature measurements of the bottom surface $T_B(t_n)$ of the wafer.

The process (500) can then start storing temperature measurement data a predetermined time after (e.g., 50 milliseconds) after the process control system indicates application of a thermal heat flux profile is completed as shown at (506). The process can stop storing temperature measurement data when the process control system indicates wafer temperatures $T_T(t_n)$ and $T_B(t_n)$ are below a temperature where the wafer can be removed as shown at (508).

The process (500) can include dividing measurement data into sets spanning N predetermined time intervals. For each time interval, two sets of cooling model parameter values and/or model fitting error metrics (e.g., root mean square error) are estimated (510). One set can be based on the temperature measurements of the top surface $T_T(t_n)$. Another set can be based on temperature measurements of the bottom surface $T_B(t_n)$. The cooling model parameter values can include, for instance, an exponential cooling constant in Newton's law of cooling.

The process (500) can then determine whether the mean and/or standard deviation values of all chosen estimated model parameters across the time intervals are within an acceptable range associated with a non-broken wafer (512). If so, the control system can provide a signal indicating that the wafer is not broken (514). If the estimated model parameters are not within the acceptable range, the control system can provide a signal indicating that the wafer is broken (516). The process can then include performing corrective actions (518), such as sending a signal to a process control system to prevent the next wafer from being loaded into the chamber and remediating the broken wafer from the chamber.

As shown in FIG. 15, this process (500) can continue until it is determined at (420) the last wafer is processed, at which point the process ends. If the last wafer has not been processed, the process (500) can include processing the next wafer (522).

An advantage of the example processes for wafer breakage detection according to example embodiments of the present disclosure is that it can be implemented using temperature measurement and control systems found in millisecond anneal systems without requiring additional hardware or hardware modifications. For instance, the wafer breakage detection processes according to example aspects of the present disclosure can use the existing measurements of the top and bottom of the wafer, which are based on radiation thermally emitted from the central region of the wafer. The measurements can be processed using additions and/or modifications to the software implemented control algorithms.

While the present subject matter has been described in detail with respect to specific example embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A temperature measurement system for a millisecond anneal system, the temperature measurement system comprising:
   a first temperature sensor configured to obtain temperature measurements associated with a top surface of a semiconductor substrate in a millisecond anneal system;
   a second temperature sensor configured to obtain temperature measurements associated with a bottom surface of a semiconductor substrate in a millisecond anneal system;
   at least one processing circuit configured to perform operations, the operations comprising:
      accessing data indicative of temperature measurements obtained from the first temperature sensor and the second temperature sensor during a cool down period following application of a millisecond anneal pulse to the semiconductor substrate;
      estimating one or more metrics associated with a cooling model based at least in part on the data indicative of the plurality of temperature measurements; and
      determining a breakage detection signal based at least in part on the one or more metrics associated with the cooling model, the breakage detection signal indicative of whether the semiconductor substrate has broken during thermal processing.

2. The temperature measurement system of claim 1, wherein the first temperature sensor and the second temperature sensor are configured to measure temperature by measuring radiation from the semiconductor substrate.

3. The temperature measurement system of claim 1, wherein the one or more metrics comprise a cooling model parameter or a model fitting error.

4. The temperature measurement system of claim 3, wherein the cooling model parameter comprises an exponential cooling constant in Newton's law of cooling.

5. A millisecond anneal system, comprising:
   a processing chamber;
   a wafer plane plate configured to support a semiconductor substrate, the wafer plane plate dividing the process chamber into a top chamber and a bottom chamber;
   one or more heat sources configured to provide a millisecond anneal pulse to a top surface of the semiconductor substrate;
   a first temperature sensor configured to obtain temperature measurements associated the top surface of semiconductor substrate;
   a second temperature sensor configured to obtain temperature measurements associated with the bottom surface of the semiconductor substrate;
   at least one processing circuit configured to perform operations, the operations comprising:
      accessing data indicative of temperature measurements obtained from the first temperature sensor and the second temperature sensor during a cool down period following application of the millisecond anneal pulse to the semiconductor substrate;
      estimating one or more metrics associated with a cooling model based at least in part on the data indicative of the plurality of temperature measurements; and
      determining a breakage detection signal based at least in part on the one or more metrics associated with the cooling model, the breakage detection signal indicative of whether the semiconductor substrate has broken during thermal processing.

\* \* \* \* \*